United States Patent
Wurster et al.

(10) Patent No.: US 7,582,063 B2
(45) Date of Patent: Sep. 1, 2009

(54) BLOOD TESTING APPARATUS HAVING A ROTATABLE CARTRIDGE WITH MULTIPLE LANCING ELEMENTS AND TESTING MEANS

(75) Inventors: Thomas Wurster, Heidenheim (DE); Krzysztof D. Malowaniec, Heidenheim (DE); Christoph Diekmann, Heidenheim (DE)

(73) Assignee: Pelikan Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/432,061

(22) PCT Filed: Nov. 21, 2001

(86) PCT No.: PCT/EP01/13514

§ 371 (c)(1),
(2), (4) Date: May 19, 2003

(87) PCT Pub. No.: WO02/41779

PCT Pub. Date: May 30, 2002

(65) Prior Publication Data

US 2004/0039303 A1  Feb. 26, 2004

(30) Foreign Application Priority Data

Nov. 21, 2000  (DE) ................. 100 57 832

(51) Int. Cl.
*A61B 5/00* (2006.01)
*B65D 81/00* (2006.01)
(52) U.S. Cl. .............. 600/584; 600/583; 606/182
(58) Field of Classification Search .......... 600/573, 600/575, 576, 583, 584; 606/181–183
See application file for complete search history.

(56) References Cited

U.S. PATENT DOCUMENTS

| | | | |
|---|---|---|---|
| 2,801,633 A | 8/1957 | Mauze et al. | |
| 4,338,174 A | 7/1982 | Tamura | 204/195 |
| 4,420,564 A | 12/1983 | Tsuji | 435/288 |
| 4,590,411 A | 5/1986 | Kelly | 318/687 |
| 4,627,445 A | 12/1986 | Garcia | |
| 4,637,393 A | 1/1987 | Ray | 128/305 |
| 4,758,323 A | 7/1988 | Davis | 204/403 |
| 4,787,398 A | 11/1988 | Garcia | |
| 4,794,926 A * | 1/1989 | Munsch et al. | 606/183 |
| 4,886,499 A | 12/1989 | Cirelli | 604/131 |

(Continued)

FOREIGN PATENT DOCUMENTS

DE  4420232  12/1995

(Continued)

*Primary Examiner*—Max Hindenburg
*Assistant Examiner*—Jonathan M Foreman
(74) *Attorney, Agent, or Firm*—Paul Davis; Goodwin Procter LLP

(57) ABSTRACT

A blood testing apparatus includes a device for withdrawing blood, a membrane-type testing element, an evaluating device, and a display device forming a complete system which can be manipulated as a single piece of apparatus. Multiple testing elements can be inserted into the apparatus and brought successively to a work position for carrying out several measurements. The blood withdrawing device includes multiple pricking elements. One pricking element is pushed through one testing element and pricks the surface of the skin of a user. The pricking position is disposed so that blood withdrawn from the surface of the skin can impinge upon the testing element.

16 Claims, 5 Drawing Sheets

U.S. PATENT DOCUMENTS

| | | | |
|---|---|---|---|
| 4,924,879 A | 5/1990 | O'Brien | |
| 4,999,582 A | 3/1991 | Parks | 324/438 |
| 5,019,974 A | 5/1991 | Beckers | 364/413.02 |
| 5,029,583 A | 7/1991 | Meserol | |
| 5,035,704 A | 7/1991 | Lambert et al. | |
| 5,047,044 A | 9/1991 | Smith et al. | |
| 5,108,889 A | 4/1992 | Smith et al. | |
| 5,178,142 A | 1/1993 | Harjunmaa | 128/633 |
| 5,181,910 A | 1/1993 | Scanlon | 604/67 |
| 5,181,914 A | 1/1993 | Zook | 604/307 |
| 5,183,042 A | 2/1993 | Harjunmaa | 128/633 |
| 5,216,597 A | 6/1993 | Beckers | 364/413.02 |
| 5,228,972 A | 7/1993 | Osaka | 204/415 |
| 5,251,126 A | 10/1993 | Kahn | 364/413.11 |
| 5,277,181 A | 1/1994 | Mendelson | 128/633 |
| 5,312,590 A | 5/1994 | Gunasingham | 422/56 |
| 5,352,351 A | 10/1994 | White | 204/406 |
| 5,371,687 A | 12/1994 | Holmes | 364/514 |
| 5,405,511 A | 4/1995 | White | 204/153.1 |
| 5,409,664 A | 4/1995 | Allen | |
| 5,438,271 A | 8/1995 | White | 324/444 |
| 5,507,288 A | 4/1996 | Bocker | 128/633 |
| 5,508,171 A | 4/1996 | Walling | 205/777.5 |
| 5,510,266 A * | 4/1996 | Bonner et al. | 436/43 |
| 5,514,152 A | 5/1996 | Smith | |
| 5,640,954 A | 6/1997 | Pfeiffer | 128/635 |
| 5,643,306 A * | 7/1997 | Schraga | 606/182 |
| 5,676,143 A | 10/1997 | Simonsen | 128/633 |
| 5,680,858 A | 10/1997 | Hansen et al. | 128/635 |
| 5,709,699 A | 1/1998 | Warner | 606/181 |
| 5,738,244 A | 4/1998 | Charlton et al. | 221/26 |
| 5,741,228 A | 4/1998 | Lambrecht | 604/93 |
| 5,746,898 A | 5/1998 | Preidel | 204/403 |
| 5,770,086 A | 6/1998 | Indriksons et al. | |
| 5,794,219 A | 8/1998 | Brown | 705/37 |
| 5,807,375 A | 9/1998 | Gross | 604/890.1 |
| 5,822,715 A | 10/1998 | Worthington | 702/19 |
| 5,828,943 A | 10/1998 | Brown | 434/258 |
| 5,830,219 A | 11/1998 | Bird et al. | 606/130 |
| 5,832,448 A | 11/1998 | Brown | 705/2 |
| 5,853,373 A | 12/1998 | Griffith | 600/554 |
| 5,868,135 A | 2/1999 | Kaufman | 128/630 |
| 5,871,494 A * | 2/1999 | Simons et al. | 606/181 |
| 5,879,163 A | 3/1999 | Brown | 434/236 |
| 5,879,310 A | 3/1999 | Sopp | 600/578 |
| 5,885,211 A | 3/1999 | Eppstein | 600/309 |
| 5,887,133 A | 3/1999 | Brown | 395/200.3 |
| RE36,191 E | 4/1999 | Solomon | 395/308 |
| 5,893,870 A | 4/1999 | Talen | 606/201 |
| 5,897,493 A | 4/1999 | Brown | 600/300 |
| 5,899,855 A | 5/1999 | Brown | 600/301 |
| 5,899,915 A | 5/1999 | Saadat | |
| 5,913,310 A | 6/1999 | Brown | 128/897 |
| 5,918,603 A | 7/1999 | Brown | 128/897 |
| 5,933,136 A | 8/1999 | Brown | 345/327 |
| 5,942,102 A | 8/1999 | Hodges | 205/775 |
| 5,951,300 A | 9/1999 | Brown | 434/236 |
| 5,951,492 A | 9/1999 | Douglas | |
| 5,951,493 A | 9/1999 | Douglas et al. | 600/583 |
| 5,956,501 A | 9/1999 | Brown | 395/500.32 |
| 5,960,403 A | 9/1999 | Brown | 705/2 |
| 5,964,718 A | 10/1999 | Duchon | 600/583 |
| 5,971,941 A | 10/1999 | Simons et al. | |
| 5,972,715 A | 10/1999 | Celentano | 436/164 |
| 5,974,124 A | 10/1999 | Schlueter | 379/106.02 |
| 5,985,559 A | 11/1999 | Brown | 435/6 |
| 5,997,476 A | 12/1999 | Brown | 600/300 |
| 6,015,392 A | 1/2000 | Douglas | 600/583 |
| 6,023,686 A | 2/2000 | Brown | 705/37 |
| 6,032,119 A | 2/2000 | Brown | 705/2 |
| 6,036,924 A | 3/2000 | Simons et al. | |
| 6,041,253 A | 3/2000 | Kost | 604/20 |
| 6,048,352 A | 4/2000 | Douglas | 606/181 |
| 6,056,701 A | 5/2000 | Duchon | 600/583 |
| 6,061,128 A | 5/2000 | Zweig | 356/243.4 |
| 6,066,103 A | 5/2000 | Duchon | 600/583 |
| 6,068,615 A | 5/2000 | Brown | 604/207 |
| 6,071,251 A | 6/2000 | Cunningham et al. | |
| 6,071,294 A * | 6/2000 | Simons et al. | 606/181 |
| 6,086,545 A | 7/2000 | Roe | 600/570 |
| 6,093,146 A | 7/2000 | Filangeri | 600/300 |
| 6,093,156 A | 7/2000 | Cunningham | |
| 6,101,478 A | 8/2000 | Brown | 705/2 |
| 6,113,578 A | 9/2000 | Brown | 604/207 |
| 6,122,536 A | 9/2000 | Sun | 600/341 |
| 6,144,837 A | 11/2000 | Quy | 434/307 R |
| 6,151,586 A | 11/2000 | Brown | 705/14 |
| 6,155,267 A | 12/2000 | Nelson | 128/899 |
| 6,161,095 A | 12/2000 | Brown | 705/2 |
| 6,167,362 A | 12/2000 | Brown | 703/11 |
| 6,167,386 A | 12/2000 | Brown | 705/37 |
| 6,168,563 B1 | 1/2001 | Brown | 600/301 |
| 6,171,325 B1 | 1/2001 | Mauze et al. | 606/171 |
| 6,177,931 B1 | 1/2001 | Alexander et al. | |
| 6,186,145 B1 | 2/2001 | Brown | 128/897 |
| 6,210,272 B1 | 4/2001 | Brown | 463/1 |
| 6,228,100 B1 * | 5/2001 | Schraga | 606/183 |
| 6,233,471 B1 | 5/2001 | Berner | 600/345 |
| 6,233,539 B1 | 5/2001 | Brown | 703/11 |
| 6,240,393 B1 | 5/2001 | Brown | 705/1 |
| 6,246,992 B1 | 6/2001 | Brown | 705/2 |
| 6,248,065 B1 | 6/2001 | Brown | 600/300 |
| 6,261,519 B1 | 7/2001 | Harding | |
| 6,270,455 B1 | 8/2001 | Brown | 600/300 |
| 6,294,897 B1 | 9/2001 | Champlin | 320/153 |
| 6,302,844 B1 | 10/2001 | Walker | 600/300 |
| 6,305,804 B1 | 10/2001 | Rice | 351/221 |
| 6,315,738 B1 | 11/2001 | Nishikawa | |
| 6,329,161 B1 | 12/2001 | Heller | 435/14 |
| 6,330,426 B2 | 12/2001 | Brown | 434/307 R |
| 6,334,778 B1 | 1/2002 | Brown | 434/258 |
| 6,349,229 B1 | 2/2002 | Watanabe | 600/345 |
| 6,368,273 B1 | 4/2002 | Brown | 600/300 |
| 6,375,469 B1 | 4/2002 | Brown | 434/236 |
| 6,381,577 B1 | 4/2002 | Brown | 705/2 |
| 6,423,014 B1 | 7/2002 | Churchill et al. | |
| 6,464,649 B1 | 10/2002 | Duchon | 600/583 |
| 6,472,220 B1 * | 10/2002 | Simons et al. | 436/63 |
| 6,477,394 B2 | 11/2002 | Rice | 600/318 |
| 6,477,424 B1 | 11/2002 | Thompson | 607/60 |
| 6,494,830 B1 | 12/2002 | Wessel | 600/300 |
| 6,503,381 B1 | 1/2003 | Gotoh | 204/403.14 |
| 6,530,892 B1 * | 3/2003 | Kelly | 600/583 |
| 6,537,207 B1 | 3/2003 | Rice | 600/121 |
| 6,541,266 B2 | 4/2003 | Modzelewski | 436/95 |
| 6,553,244 B2 | 4/2003 | Lesho | 600/347 |
| 6,554,381 B2 | 4/2003 | Locher | 347/7 |
| 6,558,320 B1 | 5/2003 | Causey | 600/300 |
| 6,558,402 B1 | 5/2003 | Chelak | 606/182 |
| 6,560,471 B1 | 5/2003 | Heller | 600/347 |
| 6,561,978 B1 | 5/2003 | Conn | 600/309 |
| 6,562,210 B1 | 5/2003 | Bhullar | 204/403.3 |
| 6,565,509 B1 | 5/2003 | Say et al. | 600/365 |
| 6,575,905 B2 | 6/2003 | Knobbe | 600/365 |
| 6,576,117 B1 | 6/2003 | Iketaki et al. | 205/777.5 |
| 6,582,573 B2 | 6/2003 | Douglas | 204/403.1 |
| 6,595,919 B2 | 7/2003 | Berner | 600/365 |
| 6,604,050 B2 | 8/2003 | Trippel | 702/19 |
| 6,607,494 B1 | 8/2003 | Fowler | 600/570 |
| 6,638,772 B1 | 10/2003 | Douglas | 436/518 |
| 6,645,142 B2 | 11/2003 | Braig | 600/300 |
| 6,645,219 B2 | 11/2003 | Roe | 606/182 |
| 6,650,915 B2 | 11/2003 | Routt | 600/319 |
| 6,671,527 B2 | 12/2003 | Peterson | 600/316 |

| Patent | Date | Name | Class |
|---|---|---|---|
| 6,706,049 B2 | 3/2004 | Moerman | 606/181 |
| 6,706,159 B2 * | 3/2004 | Moerman et al. | 204/403.03 |
| 6,721,586 B2 | 4/2004 | Kiser | 600/345 |
| 6,723,046 B2 | 4/2004 | Lichtenstein | 600/300 |
| 6,743,635 B2 | 6/2004 | Neel | 436/95 |
| 6,749,618 B2 | 6/2004 | Levaughn | 606/182 |
| 6,764,496 B2 | 7/2004 | Schraga | 606/182 |
| 6,780,647 B2 | 8/2004 | Fujiwara | 436/169 |
| 6,783,537 B1 * | 8/2004 | Kuhr et al. | 606/182 |
| 6,787,109 B2 | 9/2004 | Haar | 422/82.05 |
| 6,808,499 B1 | 10/2004 | Churchill | 600/587 |
| 6,811,406 B2 | 11/2004 | Grubge | |
| 6,844,149 B2 | 1/2005 | Goldman | 435/4 |
| 6,849,052 B2 | 2/2005 | Uchigaki et al. | |
| 6,869,418 B2 | 3/2005 | Marano-Ford | 604/192 |
| 6,872,200 B2 | 3/2005 | Mann | 604/890.1 |
| 6,875,208 B2 | 4/2005 | Santini | 604/890.1 |
| 6,875,223 B2 | 4/2005 | Argauer | 606/181 |
| 6,875,613 B2 | 4/2005 | Shartle | 436/63 |
| 6,878,120 B2 | 4/2005 | Roe | 600/583 |
| 6,878,251 B2 | 4/2005 | Hodges | 204/403.14 |
| 6,878,255 B1 | 4/2005 | Wang | 204/452 |
| 6,878,262 B2 | 4/2005 | Taniike | 205/777.5 |
| 6,880,968 B1 | 4/2005 | Haar | 374/131 |
| 6,881,203 B2 | 4/2005 | Delmore | 604/272 |
| 6,881,322 B2 | 4/2005 | Tokunaga | 205/775 |
| 6,881,378 B1 | 4/2005 | Zimmer | 422/58 |
| 6,881,541 B2 | 4/2005 | Petersen et al. | |
| 6,881,550 B2 | 4/2005 | Phillips | 435/14 |
| 6,881,551 B2 | 4/2005 | Heller | 435/14 |
| 6,881,578 B2 | 4/2005 | Otake | 436/44 |
| 6,882,940 B2 | 4/2005 | Potts | 702/23 |
| 6,884,592 B2 | 4/2005 | Matzinger | 435/7.1 |
| 6,885,196 B2 | 4/2005 | Taniike | 324/444 |
| 6,885,883 B2 | 4/2005 | Parris | 600/347 |
| 6,887,239 B2 | 5/2005 | Elstrom | 606/41 |
| 6,887,253 B2 | 5/2005 | Schraga | 606/182 |
| 6,887,254 B1 | 5/2005 | Curie | 606/181 |
| 6,887,426 B2 | 5/2005 | Phillips | 422/56 |
| 6,887,709 B2 | 5/2005 | Leong | 436/8 |
| 6,889,069 B2 | 5/2005 | Routt | 600/319 |
| 6,890,319 B1 | 5/2005 | Crocker | 604/131 |
| 6,890,421 B2 | 5/2005 | Ohara | 205/777.5 |
| 6,890,484 B2 | 5/2005 | Bautista | 422/58 |
| 6,891,936 B2 | 5/2005 | Kai | 379/106.02 |
| 6,892,085 B2 | 5/2005 | McIvor | 600/347 |
| 6,893,396 B2 | 5/2005 | Schulze | 600/300 |
| 6,893,545 B2 | 5/2005 | Gotoh | 204/403.5 |
| 6,893,552 B1 | 5/2005 | Wang | 205/777.5 |
| 6,895,263 B2 | 5/2005 | Shin | 600/316 |
| 6,895,264 B2 | 5/2005 | Rice | 600/319 |
| 6,895,265 B2 | 5/2005 | Silver | 600/345 |
| 6,896,793 B2 | 5/2005 | Erdosy | 205/775 |
| 6,897,788 B2 | 5/2005 | Khair | 340/870.16 |
| 6,902,905 B2 | 6/2005 | Burson | 435/14 |
| 6,904,301 B2 | 6/2005 | Raskas | 600/310 |
| 6,905,733 B2 | 6/2005 | Russel | 427/393.5 |
| 6,908,008 B2 | 6/2005 | Pugh | 221/135 |
| 6,908,535 B2 | 6/2005 | Rankin | 204/406 |
| 6,908,591 B2 | 6/2005 | MacPhee | 422/22 |
| 6,908,593 B1 | 6/2005 | Shartle | 422/58 |
| 6,911,130 B2 | 6/2005 | Brenneman | 204/400 |
| 6,911,131 B2 | 6/2005 | Miyazaki | 204/403.14 |
| 6,911,621 B2 | 6/2005 | Bhullar | 219/121.69 |
| 6,916,410 B2 | 7/2005 | Katsuki | 204/403 |
| 6,918,874 B1 | 7/2005 | Hatch et al. | 600/365 |
| 6,918,901 B1 | 7/2005 | Theeuwes et al. | |
| 6,918,918 B1 | 7/2005 | Schraga | 606/182 |
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |
| 6,925,393 B1 | 8/2005 | Kalatz | 702/27 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,953,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |
| 6,960,287 B2 | 11/2005 | Charlton | 205/775 |
| 6,960,289 B2 | 11/2005 | Hodges | 205/778 |
| 6,964,871 B2 | 11/2005 | Bell | 436/95 |
| 6,965,791 B1 | 11/2005 | Hitchcock | 600/345 |
| 6,966,880 B2 | 11/2005 | Boecker | 600/583 |
| 6,966,977 B2 | 11/2005 | Hasegawa | 204/403.07 |
| 6,967,105 B2 | 11/2005 | Nomura | 436/169 |
| 6,968,375 B1 | 11/2005 | Brown | 709/224 |
| 6,969,359 B2 | 11/2005 | Duchon | 600/583 |
| 6,969,450 B2 | 11/2005 | Taniike | 204/403.01 |
| 6,969,451 B2 | 11/2005 | Shin | 204/412 |
| 6,973,706 B2 | 12/2005 | Say | 29/595 |
| 6,975,893 B2 | 12/2005 | Say | 600/347 |
| 6,977,032 B2 | 12/2005 | Hasegawa | 204/403.05 |
| 6,979,544 B2 | 12/2005 | Keen | 435/6 |
| 6,979,571 B2 | 12/2005 | Modzelewski | 436/164 |
| 6,982,027 B2 | 1/2006 | Yagi | 204/403.06 |
| 6,982,431 B2 | 1/2006 | Modlin et al. | |
| 6,983,176 B2 | 1/2006 | Gardner | 600/310 |
| 6,983,177 B2 | 1/2006 | Rule | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 | 1/2006 | Roe | 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/345 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |

| Patent No. | Date | Name | Class |
|---|---|---|---|
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,044,911 B2 | 5/2006 | Drinan | 600/300 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D523,555 S | 6/2006 | Loerwald | D24/146 |
| 7,056,425 B2 | 6/2006 | Hasegawa | 204/403.04 |
| 7,056,495 B2 | 6/2006 | Roser | 424/45 |
| 7,058,437 B2 | 6/2006 | Buse | 600/347 |
| 7,060,059 B2 | 6/2006 | Keith | 604/504 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,066 B2 | 9/2006 | Schraga | 606/182 |
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorezyk | 205/792 |
| 7,144,496 B2 | 12/2006 | Meserol | 205/792 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,160,251 B2 | 1/2007 | Neel | 600/365 |
| 7,160,313 B2 | 1/2007 | Galloway | 606/167 |
| 7,160,678 B1 | 1/2007 | Kayyem et al. | |
| 7,163,616 B2 | 1/2007 | Vreeke | 205/777.5 |
| 7,166,074 B2 | 1/2007 | Reghabi | 600/365 |
| 7,167,734 B2 | 1/2007 | Khalil | 600/310 |
| 7,167,818 B2 | 1/2007 | Brown | 703/11 |
| 7,225,535 B2 | 6/2007 | Feldman et al. | |
| 7,226,461 B2 | 6/2007 | Boecker et al. | |
| 2001/0011157 A1 | 8/2001 | Latterell | 600/576 |
| 2001/0016682 A1 | 8/2001 | Berner | 600/345 |
| 2002/0016606 A1 | 2/2002 | Moerman | 606/181 |
| 2002/0019748 A1 | 2/2002 | Brown | 705/2 |
| 2002/0042594 A1 | 4/2002 | Lum et al. | |
| 2002/0078091 A1 | 6/2002 | Vu | 707/513 |
| 2002/0081559 A1 | 6/2002 | Brown | 434/307 R |
| 2002/0087056 A1 | 7/2002 | Aceti | |

| Pub. No. | Date | Inventor | Class |
|---|---|---|---|
| 2002/0120261 A1 | 8/2002 | Morris | 606/41 |
| 2002/0130042 A1 | 9/2002 | Moerman et al. | 204/403.01 |
| 2002/0133377 A1 | 9/2002 | Brown | 705/3 |
| 2002/0137998 A1 | 9/2002 | Smart | 600/347 |
| 2002/0138040 A1 | 9/2002 | Flora | 604/116 |
| 2003/0028125 A1 | 2/2003 | Yuzhakov | |
| 2003/0050537 A1 | 3/2003 | Wessel | 600/300 |
| 2003/0069753 A1 | 4/2003 | Brown | 705/2 |
| 2003/0083685 A1 | 5/2003 | Freeman et al. | |
| 2003/0083686 A1 | 5/2003 | Freeman | |
| 2003/0088160 A1 | 5/2003 | Halleck | 600/300 |
| 2003/0135333 A1 | 7/2003 | Aceti | 702/31 |
| 2003/0139653 A1 | 7/2003 | Manser | 600/300 |
| 2003/0149348 A1 | 8/2003 | Raskas | 600/310 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0199895 A1 | 10/2003 | Boecker | 606/181 |
| 2003/0212579 A1 | 11/2003 | Brown | 705/2 |
| 2003/0225317 A1 | 12/2003 | Schell | 600/300 |
| 2003/0229514 A2 | 12/2003 | Brown | 705/2 |
| 2004/0009100 A1 | 1/2004 | Simons | 422/102 |
| 2004/0019259 A1 | 1/2004 | Brown | 600/300 |
| 2004/0039342 A1 | 2/2004 | Eppstein | 604/200 |
| 2004/0039408 A1 | 2/2004 | Abulhaj | 606/181 |
| 2004/0049219 A1 | 3/2004 | Briggs | 606/181 |
| 2004/0049220 A1 | 3/2004 | Boecker | 606/181 |
| 2004/0050694 A1 | 3/2004 | Yang | 204/403.02 |
| 2004/0087990 A1 | 5/2004 | Boecker | 606/181 |
| 2004/0092842 A1 | 5/2004 | Boecker | 600/575 |
| 2004/0092994 A1 | 5/2004 | Briggs | 606/181 |
| 2004/0092995 A1 | 5/2004 | Boecker | 606/181 |
| 2004/0098009 A1 | 5/2004 | Boecker | 606/181 |
| 2004/0102803 A1 | 5/2004 | Boecker | 606/183 |
| 2004/0106855 A1 | 6/2004 | Brown | 600/301 |
| 2004/0107116 A1 | 6/2004 | Brown | 705/2 |
| 2004/0116780 A1 | 6/2004 | Brown | 600/300 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0127818 A1 | 7/2004 | Roe | 600/583 |
| 2004/0137640 A1 | 7/2004 | Hirao | 436/514 |
| 2004/0193377 A1 | 9/2004 | Brown | 702/19 |
| 2004/0199409 A1 | 10/2004 | Brown | 705/3 |
| 2004/0202576 A1 | 10/2004 | Aceti | 422/82.05 |
| 2004/0219500 A1 | 11/2004 | Brown | 434/307 R |
| 2004/0220564 A1 | 11/2004 | Ho | 606/47 |
| 2004/0236362 A1 | 11/2004 | Schraga | 606/181 |
| 2004/0249254 A1 | 12/2004 | Racchini | 600/347 |
| 2004/0256228 A1 | 12/2004 | Huang | 204/434 |
| 2004/0267160 A9 | 12/2004 | Perez | 600/583 |
| 2005/0004437 A1 | 1/2005 | Kaufmann | 600/300 |
| 2005/0027181 A1 | 2/2005 | Goode et al. | |
| 2005/0027211 A1 | 2/2005 | Kuhr | 600/583 |
| 2005/0027562 A1 | 2/2005 | Brown | 705/2 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Nakahara et al. | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Schraga | 606/182 |
| 2005/0038465 A1 | 2/2005 | Schraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049473 A1 | 3/2005 | Desai | 600/347 |
| 2005/0050859 A1 | 3/2005 | Coppeta | 53/471 |
| 2005/0054082 A1 | 3/2005 | Pachl | 435/287.2 |
| 2005/0059895 A1 | 3/2005 | Brown | 600/481 |
| 2005/0060194 A1 | 3/2005 | Brown | 705/2 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Grundel | 204/403.2 |
| 2005/0098433 A1 | 5/2005 | Grundel | 204/403.2 |
| 2005/0098434 A1 | 5/2005 | Grundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowiez | 705/1 |
| 2005/0114444 A1 | 5/2005 | Brown | 709/203 |
| 2005/0118056 A1 | 6/2005 | Swanson | 423/23 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137536 A1 | 6/2005 | Gonnelli | 604/264 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0150762 A1 | 7/2005 | Butters | 204/403 |
| 2005/0150763 A1 | 7/2005 | Butters | 204/403 |

| Publication No. | Date | Name | Class |
|---|---|---|---|
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Saito | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/316 |
| 2005/0203364 A1 | 9/2005 | Monfre | 600/365 |
| 2005/0204939 A1 | 9/2005 | Krejci | 101/129 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030788 A1 | 2/2006 | Wong | 600/583 |
| 2006/0034728 A1 | 2/2006 | Kloepfer | 422/68.1 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |

| Publication No. | Date | Name | Class |
|---|---|---|---|
| 2006/0094986 A1 | 5/2006 | Neel | 600/583 |
| 2006/0095061 A1 | 5/2006 | Trautman | 606/185 |
| 2006/0096859 A1 | 5/2006 | Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olsen | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0161078 A1 | 7/2006 | Schraga | 600/583 |
| 2006/0161194 A1 | 7/2006 | Freeman | 606/185 |
| 2006/0166302 A1 | 7/2006 | Clarke | 435/25 |
| 2006/0167382 A1 | 7/2006 | Deshmukh | 600/583 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | Levaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0231396 A1 | 10/2006 | Yamaoka | 204/403.14 |
| 2006/0231418 A1 | 10/2006 | Harding | 205/775 |
| 2006/0231442 A1 | 10/2006 | Windus-Smith | 206/438 |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | Levaughn | 606/182 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna | 606/181 |
| 2006/0271083 A1 | 11/2006 | Boecker | 606/181 |
| 2006/0271084 A1 | 11/2006 | Schraga | 606/182 |
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0282109 A1 | 12/2006 | Jansen | 606/181 |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |
| 2007/0004990 A1 | 1/2007 | Kistner | 600/583 |
| 2007/0007183 A1 | 1/2007 | Schulat | 209/573 |
| 2007/0009381 A1 | 1/2007 | Schulat | 422/58 |
| 2007/0010839 A1 | 1/2007 | Galloway | 606/167 |
| 2007/0010841 A1 | 1/2007 | Teo | 606/181 |
| 2007/0015978 A1 | 1/2007 | Kanayama | 600/310 |
| 2007/0016079 A1 | 1/2007 | Freeman | 600/476 |
| 2007/0016103 A1 | 1/2007 | Calasso | 600/583 |
| 2007/0016104 A1 | 1/2007 | Jansen | 600/583 |

FOREIGN PATENT DOCUMENTS

| | | |
|---|---|---|
| DE | 10057832 C1 | 2/2002 |
| DE | 10208575 C1 | 8/2003 |
| DE | 10245721 | 12/2003 |
| DE | 10361560 A1 | 7/2005 |
| EP | 0199484 A2 | 10/1986 |
| EP | 0 364 208 A1 | 4/1990 |
| EP | 0 449 525 | 10/1991 |
| EP | 0263948 | 2/1992 |
| EP | 0 654 659 | 5/1995 |
| EP | 0 777 123 | 6/1997 |
| EP | 0 898 936 A2 | 3/1999 |
| EP | 0 951 939 | 10/1999 |

| | | | | | | |
|---|---|---|---|---|---|---|
| EP | 0 951 939 A2 | 10/1999 | | WO | WO 03/094752 | 11/2003 |
| EP | 0 964 060 | 12/1999 | | WO | WO 03/101297 | 12/2003 |
| EP | 0 985 376 | 5/2000 | | WO | WO 2004/022133 | 3/2004 |
| EP | 1 101 443 | 5/2001 | | WO | WO 2004/040285 A2 | 5/2004 |
| EP | 1101443 | 5/2001 | | WO | WO 2004/040287 A1 | 5/2004 |
| EP | 0874984 | 11/2001 | | WO | WO 2004/040948 | 5/2004 |
| EP | 01174083 | 1/2002 | | WO | WO 2004/098405 | 11/2004 |
| EP | 0759553 | 5/2002 | | WO | WO 2004/003147 | 12/2004 |
| EP | 0958495 | 11/2002 | | WO | WO 2004/107964 | 12/2004 |
| EP | 0937249 | 12/2002 | | WO | WO 2005/001418 | 1/2005 |
| EP | 01374770 | 1/2004 | | WO | WO 2005/006939 | 1/2005 |
| EP | 1502614 | 2/2005 | | WO | WO 2005/011774 | 2/2005 |
| FR | 2 555 432 A | 5/1985 | | WO | WO 2005/016125 | 2/2005 |
| GB | 233936 A | 6/1999 | | WO | WO 2005/018425 | 3/2005 |
| GB | 2335860 A | 10/1999 | | WO | WO 2005/018430 | 3/2005 |
| GB | 2335990 A | 10/1999 | | WO | WO 2005/018454 | 3/2005 |
| WO | WO 92/07263 | 4/1992 | | WO | WO 2005/018709 | 3/2005 |
| WO | WO 95/06240 | 3/1995 | | WO | WO 2005/018710 | 3/2005 |
| WO | WO 98/24373 | 6/1998 | | WO | WO 2005/018711 | 3/2005 |
| WO | WO 99/07431 A1 | 2/1999 | | WO | WO 2005/022143 | 3/2005 |
| WO | WO 99/17854 | 4/1999 | | WO | WO 2005/023088 | 3/2005 |
| WO | WO 99/18532 | 4/1999 | | WO | WO 2005/033659 | 4/2005 |
| WO | WO 99/27483 | 6/1999 | | WO | WO 2005/034720 | 4/2005 |
| WO | WO 00/06024 | 2/2000 | | WO | WO 2005/034721 | 4/2005 |
| WO | WO 00/11578 | 3/2000 | | WO | WO 2005/034741 | 4/2005 |
| WO | WO 00/15103 | 3/2000 | | WO | WO 2005/034778 | 4/2005 |
| WO | WO 00/17799 | 3/2000 | | WO | WO 2005/035017 | 4/2005 |
| WO | WO 00/17800 | 3/2000 | | WO | WO 2005/035018 | 4/2005 |
| WO | WO 00/18293 | 4/2000 | | WO | WO 2005/037095 | 4/2005 |
| WO | WO 00/19346 | 4/2000 | | WO | WO 2005/046477 | 5/2005 |
| WO | WO 00/32097 | 6/2000 | | WO | WO 2005/065399 | 7/2005 |
| WO | WO 00/32098 | 6/2000 | | WO | WO 2005/065414 | 7/2005 |
| WO | WO 00/33236 | 6/2000 | | WO | WO 2005/065415 | 7/2005 |
| WO | WO 00/42422 | 7/2000 | | WO | WO 2005/072604 | 8/2005 |
| WO | WO 00/72452 | 11/2000 | | WO | WO 2005/084557 | 9/2005 |
| WO | WO 01/15807 | 3/2001 | | WO | WO 2005/116622 | 12/2005 |
| WO | WO 01/16578 A1 | 3/2001 | | WO | WO 2005/119234 | 12/2005 |
| WO | WO 01/37174 | 5/2001 | | WO | WO 2005/121759 | 12/2005 |
| WO | WO 01/45014 A1 | 6/2001 | | WO | WO 2006/001973 | 1/2006 |
| WO | WO 01/69505 | 9/2001 | | WO | WO 2006/005545 A2 | 1/2006 |
| WO | WO 01/72220 A | 10/2001 | | WO | WO 2006/011062 | 2/2006 |
| WO | WO 02/21317 | 3/2002 | | WO | WO 2006/013045 | 2/2006 |
| WO | WO 02/25551 | 3/2002 | | WO | WO 2006/027702 A2 | 3/2006 |
| WO | WO 02/41227 | 5/2002 | | WO | WO 2006/032391 | 3/2006 |
| WO | WO 03/070099 | 8/2003 | | WO | WO 2006/072004 | 7/2006 |
| WO | WO 03/088851 A1 | 10/2003 | | * cited by examiner | | |

BLOOD TESTING APPARATUS HAVING A ROTATABLE CARTRIDGE WITH MULTIPLE LANCING ELEMENTS AND TESTING MEANS

BACKGROUND

The invention relates to a blood testing apparatus for determining an analyte, such as fructosamine, lactate, cholesterol, specifically glucose, from minimal quantities amounts of blood extracted immediately prior from a user.

The invention deals with blood testing apparatus of the kind that are configured with a membrane-like test means defining a field of measurement, said test means being wetted with the minimal amount of blood extracted and including test reagents, having an evaluation device comprising electronics working optically, preferably using reflectance analysis, or electronically and having a display device, where the aforementioned components form a complete system which can be manipulated as a single apparatus.

A diagnostic apparatus of this type is known from U.S. Pat. No. 4,787,398. This blood glucose monitoring apparatus comprises a housing structure with a push-rod arrangement to actuate a lancing element and having an evaluation device and a display device. For each measurement, a replaceable unit must be positioned in the housing structure, comprising the lancet and a test means to be wetted with blood in the form of a test strip. This replaceable unit is discarded after each use.

Using this as the point of departure, the object of the present invention is to further develop a blood testing apparatus which has fewer components to be manipulated individually and is thus easier to operate and more user friendly.

A blood testing apparatus known from EP 0 449 525 A1 similarly comprises an integral release device for a lancing element. Before each use, a new lancing element has to be manually inserted into the release device as part of the blood extraction device and then a test strip has to be inserted into the apparatus.

U.S. Pat. No. 4,627,445 shows a complete system for a glucose measuring apparatus in the aforesaid sense. But before each measurement a new replaceable unit of lancing element and test means has to be assembled to a body and removed afterwards.

U.S. Pat. No. 5,951,492 shows a similar device. According to this publication, a disposable unit comprises a capillary tube on the upper end of which a test strip is provided which is exposed to the minimal quantity of blood extracted. The capillary tube is configured at its lower end with a lancing element. Again, before and after each measurement a new disposable unit of the type just described must be installed or removed. According to a further embodiment, a transverse slot is provided in the area of the face of the apparatus facing the user, through which a porous test membrane with a carrier can be inserted, which is then penetrated by the lancing element in the lancing procedure.

According to one embodiment, U.S. Pat. No. 5,971,941 shows a complete system in the aforesaid sense, where a cartridge with unused srip-like test means is inserted into a housing and a suitable test means can then be brought into a suitable operating position by means of a driver. Through a triggering device, which forms part of the blood extraction device, a lance contained in a suitable test strip is urged outward by mean of a pushrod to pierce the surface of the user's skin so that capiliary blood can be obtained for analysis. More detailed information on how the analysis is performed cannot be obtained from this publication. According to a further embodiment described in this publication, a cylindrical disposable attachment or insert is descried which has a lancet and a tablet-shaped test membrane with an opening for the lancing device. This attachment or insert is then inserted into a recess of a pushrod arrangement which forces the lancing element outward to extract blood. Once again, before and after each test procedure the disposable unit must be installed or removed.

SUMMARY

The object, explained at the beginning, to create a user-friendly improvement of a blood testing apparatus of this type which ensures a safe supply of blood for the test means with the smallest possible quantity of blood, is achieved under the invention through a plurality of test means which can be inserted into the apparatus and brought into an operating position to perform several measurements in succession where they can interact with the evaluation device, through the blood extraction device similarly having a plurality of lancets, and when a suitable test means is positioned in the operating position, a lancet can be thrust through the test means and can pierce the surface of the user's skin which is positioned in a lancing position aligned with the operating position so that blood emanating from the skin can impinge directly on the test means.

Under the invention, installation or removal before and after each test, measurement or analysis procedure is to be avoided. For this reason, a plurality of test means and preferably a number of lancing elements corresponding exactly to number of test means is furnished in the blood testing apparatus, which can be brought into the operating position in succession and then interact with the blood extraction device when it is actuated or released. A lancing element located in the operating position is driven through the membrane-like test means and pierces the surface of a user's skin, so that the minimal quantity of blood obtained directly wets the membrane-like test means without having to penetrate capillary tubes or slots, which in turn require quantities of blood. Any number of switching and driving means powered mechanically or by an electric motor are conceivable to move the test or lancing means to the operating position and to actuate the lancing means. The number of test means, which are preferably handled as a unit, and advantageously of the lancing means as well, is preferably 5 to 75, and specifically 14–28. The numbers 14 and 28 correspond to a 2 or 4-week rhythm if one analysis is made per day.

After the evaluation and display of the result of the analysis, or of the blood glucose level, the specific test means is moved from its operating position and the next succeeding test means is brought into the operation position preferably immediately.

The lancing element could be withdrawn from the test means again before this process. It proves to be advantageous if the lancing element remains in the test means following the lancing procedure and can be removed with it from the operating position to position a new test means. The lancing element can also be retracted far enough so that it does not project beyond a finger rest area in the apparatus. However, this is not absolutely necessary.

In accordance with a further aspect of the invention, it is conceivable that the lancing element is connected to the membrane-like test means before the lancing procedure and can be inserted with it into the apparatus and moved to the operating position. The lancing element can already be inserted into the test means or be stuck through it.

Following a lancing and measurement procedure, spent lancing elements and test means can be ejected individually or together, or they can be taken to a storage and disposal position.

In a further aspect of the invention, the test means are disposed on a carrier which is movable, preferably rotatable, with respect to a housing base and inserted with the carrier into the housing base of the apparatus. The test means can then be brought in succession to the operating position by rotating the carrier or moved from the operating position to a storage and disposal position.

The test means are advantageously so disposed on the carrier that they can be positioned in a radial direction with respect to the rotatable carrier. Furthermore, the carrier preferably has an annular configuration and is carried rotatably about the center of the ring.

Protection against dirt, contamination and the effects of humidity is preferably provided. The carrier can be configured advantageously as a closed cartridge. The carrier can then have apertures which can be closed or withdrawn in the manner of a window or diaphragm to interact with the drive mechanism and allow the lancing element to extend to perform the lancing procedure or allow blood to reach the test means. As further protection, particularly against humidity, the test means can alternatively or additionally be encased in foil covers which can be removed in the operating position.

The blood extraction device is advantageously housed inside the annulus with the several lancing elements. It is conceivable that a release device, which is known in the art and described in the aforementioned publications, is housed within the annulus. For example, a pushrod-like driver arrangement is implemented, which operates on the side of a lancing element away from the body when located in the operating position such that the lancing element pierces the skin surface of a user. It would also be conceivable that a specific lancing element in the operating position is held in a wedging arrangement between the opposably movable jaws of the driving organ, so that by moving the driving organ forward and back the lancing element can be extended to the outside of the apparatus and retracted again. In any case, the drive unit of the blood extraction device, which thrusts a specific lancing element through the membrane-like test means into the skin surface of a user, forms a part of the housing or base apparatus as does the evaluation and display device. The membrane-like test means and the lancing elements, on the other hand, represent disposable elements which are inserted in a predetermined configuration, such as being located on a carrier, into the housing base.

It proves furthermore to be advantageous if, as already mentioned, the lancing elements, on a rotatable carrier, preferably on the same carrier as the test means, are inserted into the blood testing apparatus. By rotating the carrier or carriers, a specific lancing element is similarly brought into the operating position, namely into a position where it is struck by the driving organ of the blood extraction device or is gripped in a wedging arrangement and can be moved suddenly to perform the lancing procedure.

It proves to be of overall advantage if the blood testing apparatus has a basically circular disc-shaped outer contour, as it can thus be gripped and held comfortably in the user's hands.

In a further aspect of this inventive idea, the apparatus has oppositely located a lancing position for positioning the skin surface to be pierced and a release position to trigger the lancing procedure by manually actuating a release button.

The apparatus is advantageously held by a user holding the apparatus with two fingers at the lancing position and the release button. The release button has an advantegeous ergonomic shape for grasping by the thumb of a user. If preferably has a pressure point which must be overcome in order to initiate the lancing operation. For safety reasons, it proves to be advantegeous if the lancing operation can only be initiated when both fingers have taken up their correct position. This could be implemented through contact sensors or through a pressure point mechanism.

It must be pointed out that instead of a needle or lancet-shaped lancing element, which is moved preferably suddenly in the direction of the skin surface of a user to perform the lancing procedure in a manner known in the art, for example, by releasing a spring-tensioned driving device, a laser beam can also be used. The required source of laser light is among the non-disposable system components of the blood testing apparatus. With this solution as well, a specific test means can be furnished with an opening through the laser beam can pass.

In accordance with a further inventive aspect, the blood testing apparatus can be configured in the style of a wrist watch, that is to say it can have a housing base modeled after a wrist watch casing. A viewing side of the blood testing apparatus can then have a face as with a familiar watch, or a digital display. The digital display can be configured to display time and/or additional functions and to display data or information gathered by the blood testing apparatus as needed.

It can prove further advantageous if the blood testing apparatus has a removable, preferably upwardly pivotable, cover which has access to the interior of the blood testing apparatus, specifically to insert or replace the carrier for the test means and/or lancing elements. In the design of the external appearance of the blood testing apparatus in the style of a wrist watch, or even in the style of a pocket watch, it can prove advantageous if the removable or upwardly pivotable cover simultaneously comprises the face or some other time display device which is raised or pivoted upward with the cover.

In accordance with another inventive aspect, the cover when opened can reveal a view of a display device in the blood testing apparatus, which can be located either on the inward facing side of the raised cover or is revealed by the removal or upward pivoting of the cover. It can further prove to advantageous if a second removable or upwardly pivotable cover is furnished under the first removable or upwardly pivotable cover, which second cover permits or closes off access to the interior of the blood testing apparatus. This second cover could then contain the display device for the blood testing apparatus on its outer side, which can serve simultaneously as a time display. To read the data and information gathered by the blood testing apparatus, the first cover is opened so that a user can view the display device on the exposed viewing side of the second cover, or on the inner side of the first cover. The second cover is opened only to replace the test means or lancing elements.

In an aspect of the blood testing apparatus in the style of a wrist watch casing, it proves advantageous if a finger rest is furnished at the "6 o'clock" or "12 o'clock" position to perform the lancing process to draw a minimal amount of blood, or in the respective areas where the watch strap attaches. This permits convenient operability, which also has a positive effect on good wetting function, since the particular test means (when the test means are arranged essentially perpendicular to the radial direction) is aligned horizontally when the blood is extracted, which promotes even wetting.

BRIEF DESCRIPTION OF THE DRAWING

Additional features, details and advantages of the invention can be found in the appended claims and the drawing and the description to follow of a preferred embodiment of the invention.

In the drawing.

DETAILED DESCRIPTION

Figure 1:
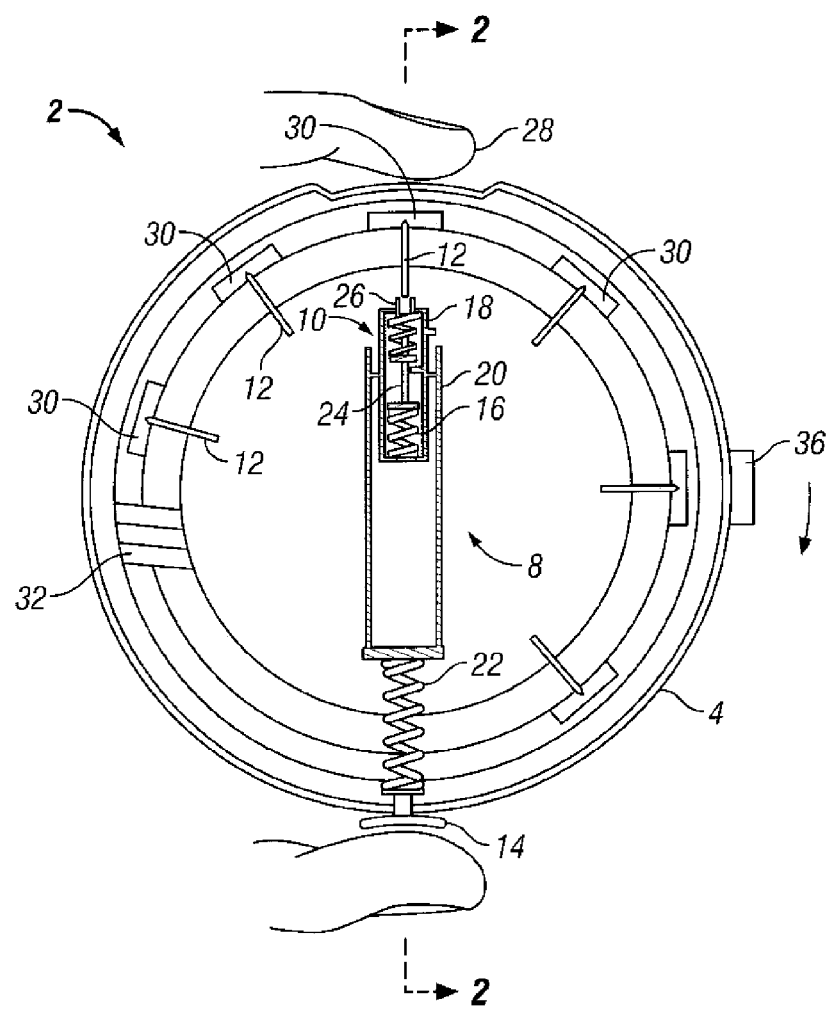
FIG. 1 shows a schematic arrangement of a first aspect of a blood testing apparatus in accordance with the invention.
Figure 2:
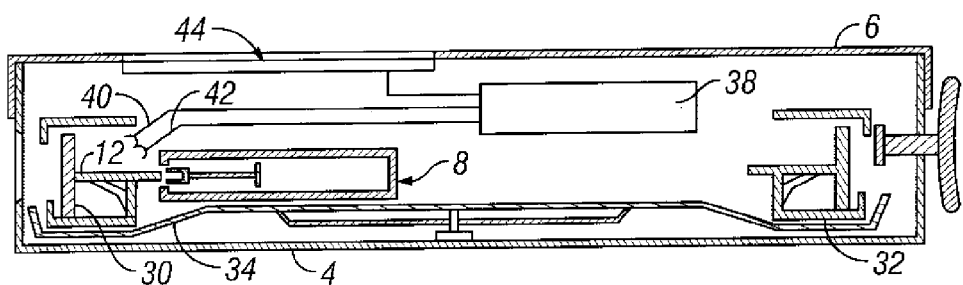
FIG. 2 shows a sectional view of the blood testing apparatus from FIG. 1.

FIGS. 1 and 2 show a schematic view of a blood testing system in accordance with the invention, where FIG. 1 represents a view into the interior with the cover removed and FIG. 2 represents a schematic sectional view. The blood testing apparatus in the form of a blood glucose measuring apparatus, identified as a whole with the reference numeral 2, comprises a housing base 4 and a removable cover 6. A blood extraction device 8 with a drive mechanism 10 and a lancing element in the form of a needle is accommodated in the interior of the housing base 4. The blood extraction device 8 interacts with a release button 14 on the narrow outer side of the disc-shaped housing base 4. The drive mechanism comprises a driving spring and a return spring 16, 18, both of which are indicated only schematically. Through mechanical coupling and control means 20, pressing the release button 14 and overcoming a pressure point mechanism 22 releases the drive mechanism 10, so that under the pre-load of the driving spring 16 a plunger 24 moves radially outward at speed, wedging the lancing element 12 between jaws 26 and driving it radially outward and immediately afterward retracting it again slightly under the effect of the return spring 18. The lancing element 12 penetrates forward briefly across the finger rest 28 lying radially opposite the release button on the outside of the housing base 4, which defines a lancing position, and briefly pierces the skin surface of a user with predetermined speed and depth of penetration to allow a minimal quantity of blood to escape.

As the lancing element 12 moves outward at speed, a membrane-like test means 30, which is located in a manner to be described in greater detail in the immediate vicinity behind the finger rest 28, is penetrated by the lancing element 12. The blood emanating from the skin surface then directly wets the outwardly facing surface of the membrane-like test means 30, which is furnished with reagents.

As can be seen from the Figures, a plurality of test means 30 is furnished with the lancing elements allocated to each of the test means 30. The test means 30 and the lancing elements 12 are located on an annular carrier 32, for example, eight or ten pairs of test means 30 and lancing elements 12 are located around the circumference or partial circumference of the annular carrier 32. With the cover 6 removed, the carrier 32 can be inserted into a locating device 34 of complementary shape which can be rotated around the center of the ring. Embodiments would also be conceivable in which the cover 6 does not need to be removed in order to insert the carrier 32, but which have a recess open to the top to insert a cassette-type closed carrier 32. This provides protection against dirt, contamination and the effects of humidity. The carrier 32 can have available apertures which can be closed and withdrawn like a window or diaphragm in order to interact with the drive mechanism and allow the lancing means to extend to the outside to perform the lancing procedure or to allow blood to reach the test means. As further protection, specifically against humidity, the test means could alternatively or additionally be covered with foil wrappers which can be removed in the operating position.

As can be seen from the Figures, the membrane-like test means 30 are disposed such that they are disposed with their surface normal in the radial direction with respect to the center of the ring. By actuating a sliding button 36 on the outside of the housing base 4, the locating device 34, and with it the carrier 32 positioned in it and held frictionally in place, are rotated into a discrete further angular position, so that the pairs of test means 30 and lancing elements 12 are brought in succession into an operating position in which the lancing element 12 can interact with the drive mechanism 10. In this way the blood glucose measuring apparatus is prepared by insertion of the preferably cassette-type carrier 32 with a number, for example, of ten test means 30 and lancing elements 12 for ten measurements. Following a measurement, the button 36 only has to be actuated to bring the next pair of test means 30 and lancing element 12 into the operating position. Additional installation and removal steps before and after a particular measuring procedure are not required. Spent test means 30 and test elements are brought in a clockwise direction with the carrier 32 to a storage or disposal position, which follows the operating position. It would also be conceivable to furnish an ejection mechanism which ejects a particular spent pair for disposal, which is regarded as less preferred since proper disposal must take place immediately. The protected arrangement of the spent pairs inside the cassette-type carrier 32 is preferred instead. After the predetermined number of tests are performed, the cassette-type-like carrier 32 is removed and disposed of and replaced with a new one.

Because the lancing element 12 penetrates the membrane-like test means 30 in the lancing process, preferably in its center, the test means 30 is ensured of being positioned in immediate proximity to the point of penetration on the skin surface of the user. The blood emanating there is immediately and, most importantly, evenly deposited on the test area of the test means 30, even when only small quantities of blood are available.

In the aspect shown, the lancing elements 12 are disposed on the carrier 32 such that they perforate the center of the test means 30 when the drive mechanism 10 acts against them. To achieve this, it can prove to be advantageous if the lancing elements 12 are disposed in such a way on the carrier 32 that the point has penetrated into the accompanying test means 30, at least partially in the direction of their thickness. This acts as an aid to positioning. A continuous guide opening can also be furnished in the test means 30. The diameter of the guide opening should preferably be smaller than the outside diameter of the lancing element 12 to prevent blood from penetrating through a gap between the outer surface of the lancing element 12 and the guide opening toward the back side of the test means 30.

An evaluation device 38 known in the art is also furnished in the interior of the glucose measuring apparatus. An optical, preferably reflectance analysis unit, is indicated schematically in FIG. 2. The evaluation device 38 can comprise a light source 40 and a sensor 42 for the reflectance measurement of the change of color of the back side of the membrane-like test means 30, where the analysis reaction of the glucose contained in the blood sample with the test or proof reagents takes place (enzymatic redox reaction). The principles of an optical analysis device are described, for example, in EP-A-0 654 659 and EP-A-0 475 692.

In the case where the electrochemical measurement principle is applied, the optical evaluation device is dispensed with. The enzymatic redox reaction is quantified instead through the detection of electrical current or voltage at an electrode (described, for example, in EP-A-0 552 223).

The evaluation device 38 comprises in a known way electronics for analysis which interact with a display device 44 which indicates, for example, in the form of an LCD display the test result, perhaps the blood glucose content. By means of the evaluation device, additional evaluation and display functions and comparisons with previously stored measurement or evaluation data could be performed, saved if necessary and their result displayed.

The blood testing apparatus under the invention thus represents a complete system which does not require the separate manipulation of test strips or lancets during the blood glucose measurement. By inserting the cassette-type carrier 32 with test means 30 and lancing elements 12, the apparatus is prepared for a specific number of measurements, for which no additional installation or removal steps or the separate manipulation of additional aids is required.

Figure 3:
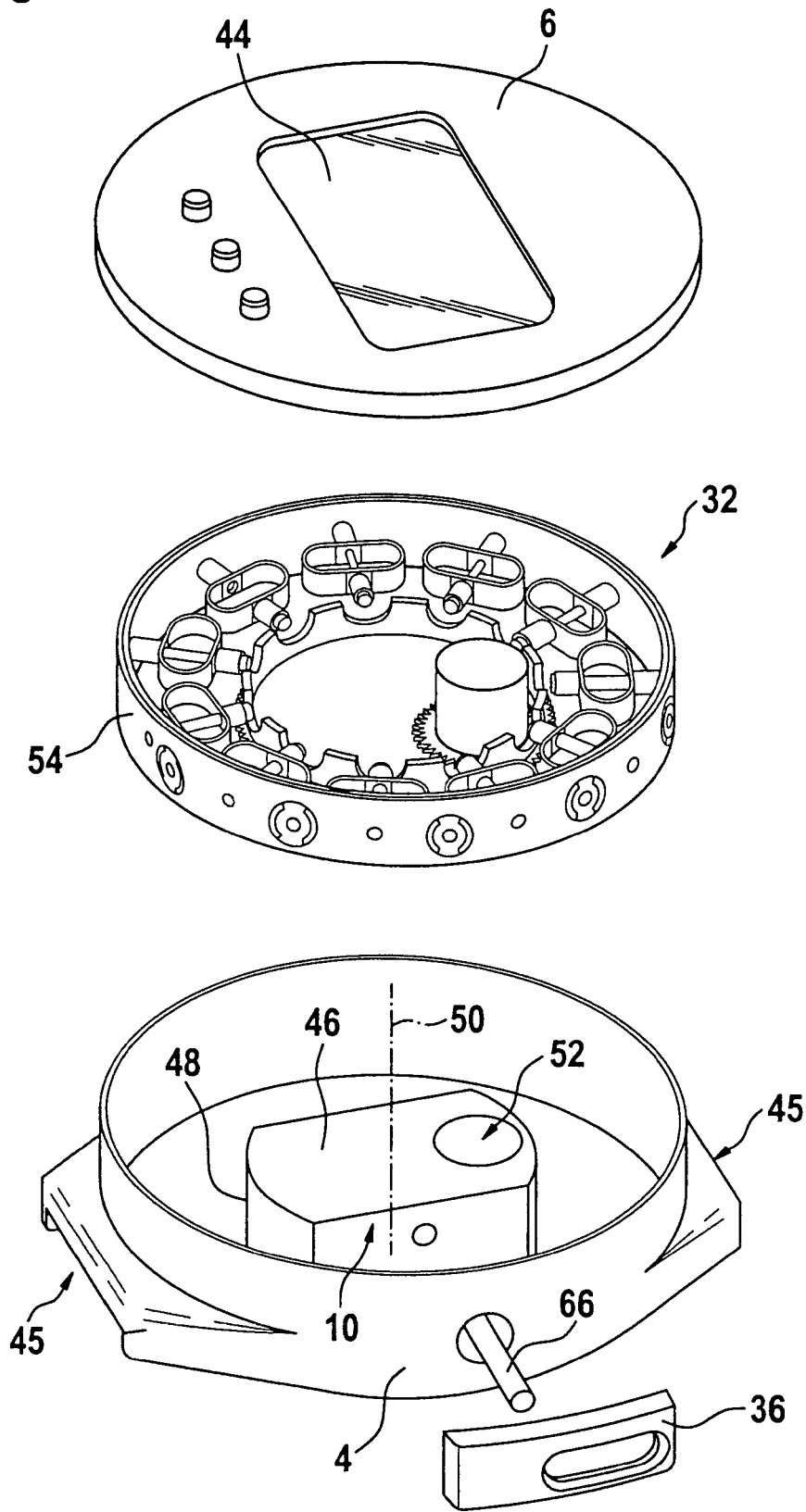
FIG. 3 shows an exploded view of a second aspect of a blood testing apparatus in accordance with the invention.
Figure 4:
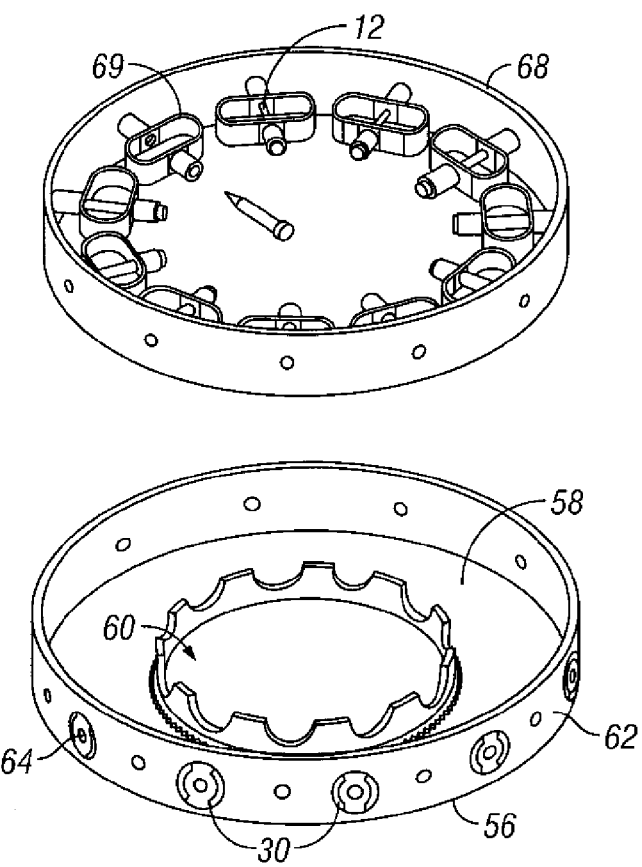
FIG. 4 shows an exploded view of the carrier for test means and lancing elements of the apparatus from FIG. 3.
Figure 5:
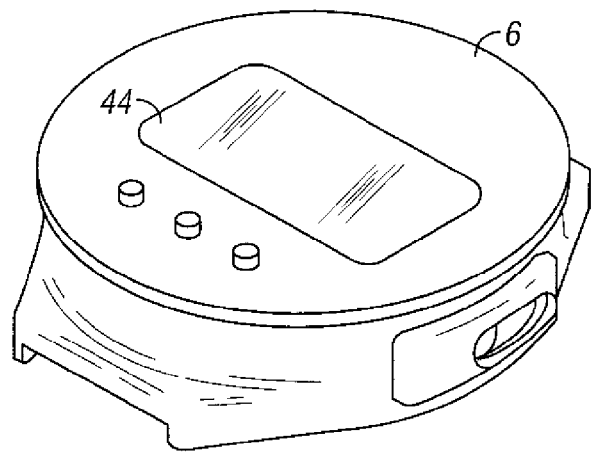
FIG. 5 shows an isometric view of the assembled blood testing apparatus from FIG. 3.

FIGS. 3 to 5 show a second aspect of the blood testing apparatus under the invention, where components identical to the first aspect are identified with the same reference numeral. In accordance with this aspect, the blood testing apparatus has a housing base 4 modeled after or approximating the basic shape of a wrist watch casing, where the dimensions, specifically the depth of the housing base 4, can be enlarged compared with traditional wrist watch casings. Further indicated are installation areas 45 for a specifically flexible pin of a normal watch strap. A dome-shaped centering means 46 is depicted in the interior of the housing base 4, which appears cuboid in plan view but which has two segmental side sections 48 which are configured concentric to an axis of rotation 50 and provide a positioning aid when inserting a carrier 32 for test means 30 and lancing elements 12. Further, a servo motor 52 (not shown in detail) is housed in the centering means 46.

The servo motor 52 can serve to move the carrier 32 to move a spent test means 30 from an operating position to a disposal position and simultaneously to position a still unused test means 30 in the operating position. It is not entirely excluded that the servo motor 52 can also serve to power the only schematically represented drive mechanism 10. The drive coupling of the servo motor 52 with the carrier 32 could, for example, be formed through a pinion gear, crown wheel, bevel gear or miter gear connection between a rotatingly driven wheel of the servo motor 52 and correspondingly configured, specifically sprocket-shaped matching gear means on the carrier 32.

As shown in FIGS. 3 and 4, the carrier 32 is configured in the shape of an annular disc-shaped cassette 54. The cassette comprises a lower housing section 56 with an annular disc-shaped floor section 58 with a circular access opening 60 and with circumferential wall section 62 running cylindrically on the outer periphery. The test means 30 are furnished in appropriate recesses 64 in the circumferential wall section 62 in a concentric arrangement around the axis of rotation 50. A similarly shaped upper housing section 68, which comprises a number of radially aligned lancing elements 12 corresponding to the number of test means 30, can be inserted into the lower housing section 56. Spring means 69 can also be seen, specifically in the form of closed loops, which hold the lancing elements 12. When the skin surface of a user is pierced, these spring elements 69 are tensioned and are able to retract the particular lancing element 12 again following the penetration through the drive mechanism 10. This arrangement of lancing elements 12 is located radially outside the aforementioned opening 60 and thus radially outside the dome-shaped centering means 46, which simultaneously comprises the drive mechanism 10 which is disposed radially inside the arrangement of lancing elements 12. The lower housing section 56 and the upper housing section 68 inserted into it are joined together so that they cannot turn and can be rotated in common as a carrier 32 around the axis 50 to bring test means 30 and lancing elements 12 into the operating position, or shift them from the operating position to a disposal position.

The button 36 schematically represented in FIG. 3 is linked to the drive mechanism 10 to actuate it. The control rod 66 suggested there running radially runs either above or below the carrier 32. As mentioned, the actuation of the drive mechanism 10 could also be achieved with a motor, preferably electrically controlled.

Finally the blood testing apparatus comprises a cover 6 which can be modeled after the face of an electronic watch and can have a display device 44, for example, in the form of an LCD display. This cover then forms the viewing side of the blood testing apparatus, as can be seen from FIG. 5.

Figure 6:
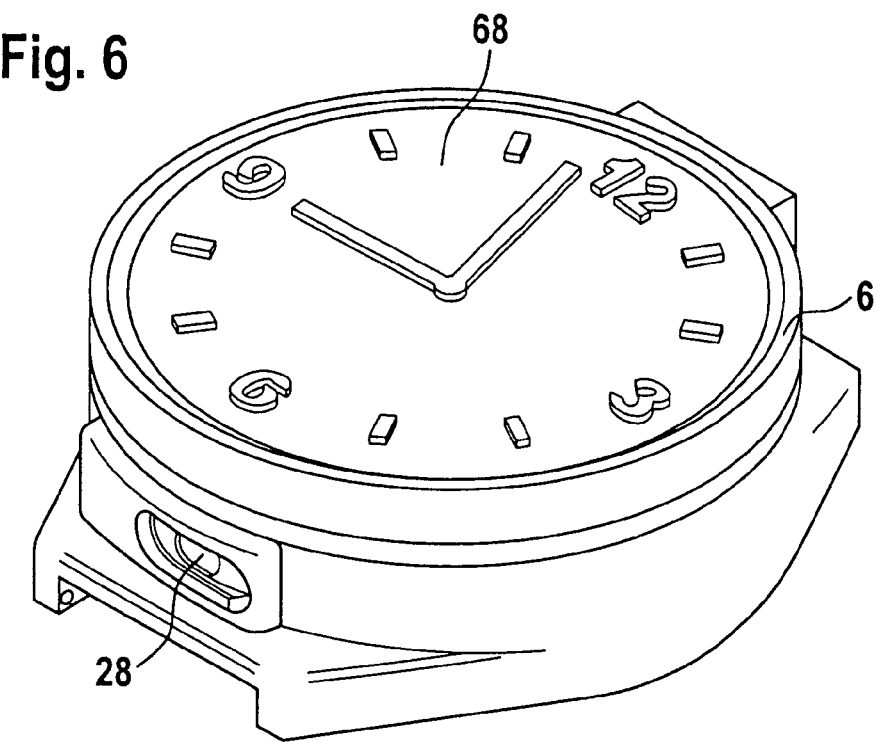
FIG. 6 shows an isometric view of a third aspect of a blood testing apparatus in accordance with the invention.

FIG. 6 shows an isometric view corresponding to FIG. 5 of a blood testing apparatus with a watch face 68 on the viewing side of a pivotally articulated cover 6. It should also be mentioned that a finger rest 28 is furnished at the "6 o'clock" position with reference to the face 68, which forms the operating position in which the skin surface is briefly penetrated by the lancing element 12 when the drive mechanism 10 is released. This arrangement proves to be advantageous insofar as the user (standing) can place the hand on the stomach when performing the lancing procedure and then position the thumb of the other hand on the finger rest 28. When the lancing process is triggered in this position, the membrane-like test means 30 is disposed essentially horizontally and the minimal amount of blood can wet the test means following gravity.

Figure 7:
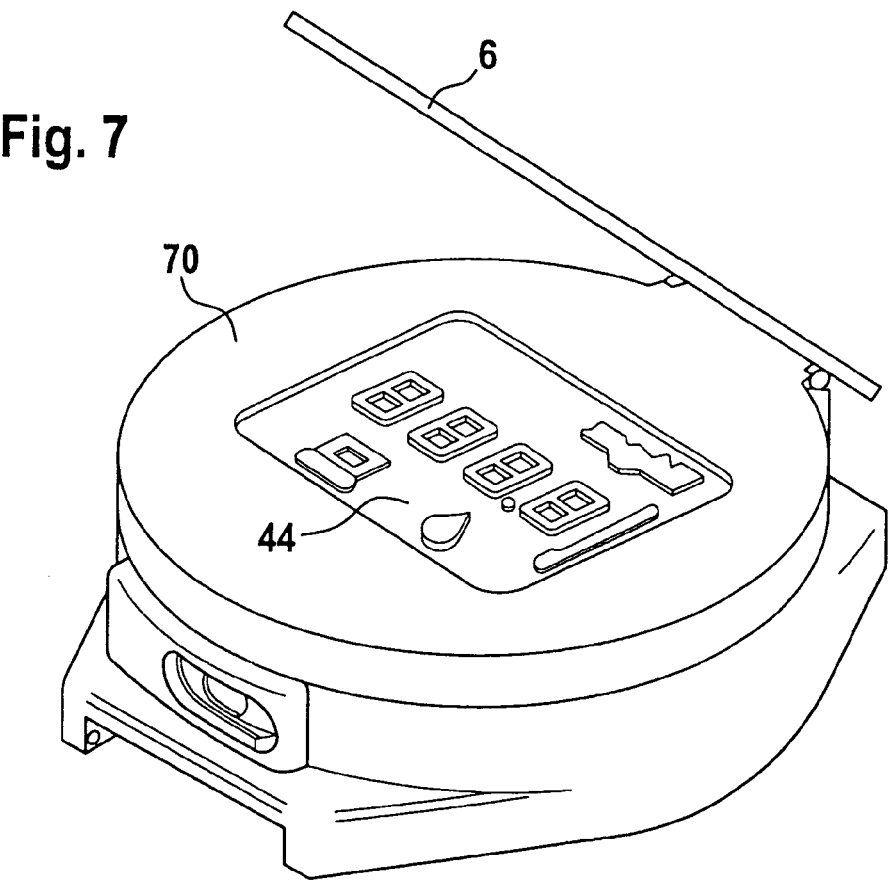
FIG. 7 shows an isometric view of the blood testing apparatus from FIG. 6 with the first cover raised.

FIG. 7 shows the blood testing apparatus from FIG. 6 with the first cover 6 pivoted up so that the view of the upper side of a second cover 70 is uncovered where, in accordance with this embodiment, the display device 44 for the blood testing apparatus is located. The display device 44 for the blood testing apparatus is thus separated spatially from the face 68 or the display unit for time. Naturally, the display device 44 could also serve to display time.

Figure 8:
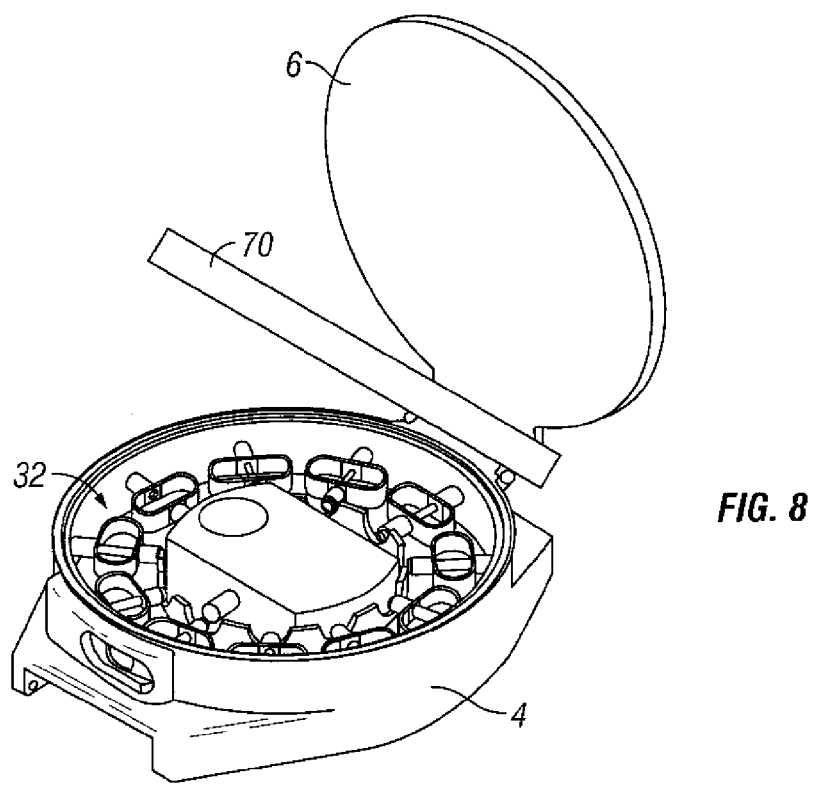
FIG. 8 shows an isometric view of the blood testing apparatus from FIG. 7 with the first and second covers raised and FIG. 9 shows an isometric view corresponding to FIG. 8 of a fourth aspect of the blood testing apparatus in accordance with the invention.

FIG. 8 shows the blood testing apparatus from FIG. 7 with the second cover 70 likewise raised so that access to the housing base 4 for inserting and removing a carrier cartridge is possible.

Figure 9:
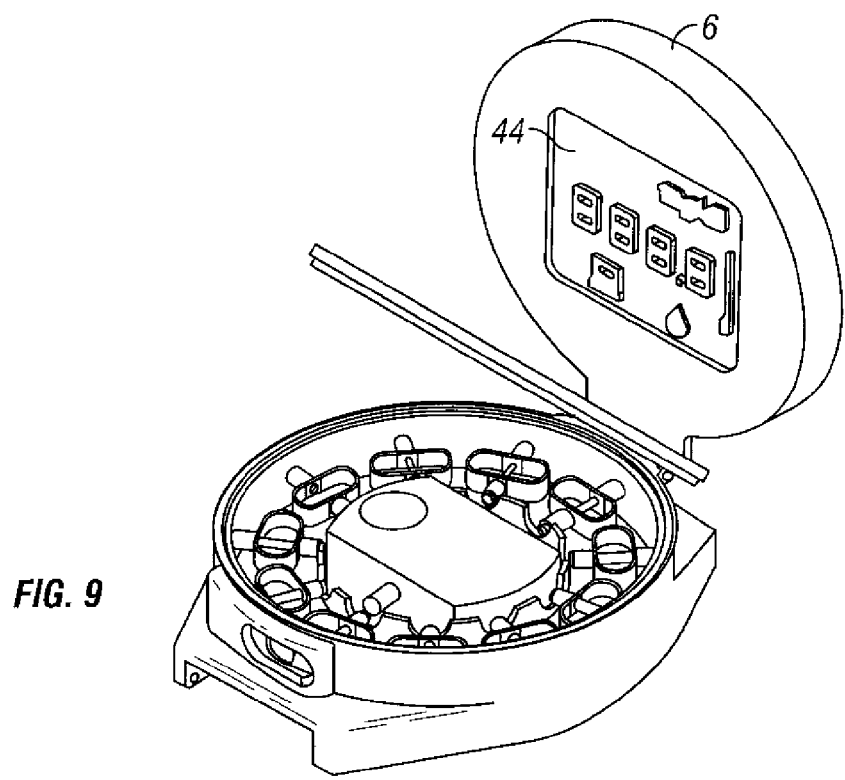

Finally, FIG. 9 shows an isometric view corresponding to FIG. 8 of a further embodiment, according to which the display device 44 for blood analysis is furnished on the inner side of the first cover 6.

What is claimed is:

1. A blood testing apparatus with a blood extraction device, comprising: a lancing element drive mechanism, a plurality of test means, positioned on a rotatable, disposable device that can be inserted into the apparatus; a plurality of lancing elements being disposed on the dispoable device such that each of a lancing element perforates through a test means when the drive mechanism acts against a lancing element, each of a lancing element being associated with a test means and prior to actuation each of a lancing element is gripped to the lancing element drive mechanism, electronics for analysis, and a display which form a complete system to be manipulated as a single apparatus, the display configured to display additional evaluation and display functions and comparisons with previously stored measurement or evaluation data, saved if desired and their results displayed if desired, wherein launch of a lancing element is initiated with a contact sensor or with a pressure point mechanism, the plurality of test means being arranged radially around an axis of rotation of the rotatable, disposable device having a circumferential wall section that runs cylindrically on an outer periphery, the test means being positioned in appropriate recesses in a circumferential wall section of the disposable device in a concentric arrangement around the axis of rotation, each of the test means and at least one lancing element having a longitudinal axis that is substantially perpendicular relative to the axis of rotation; the test means being disposed with surfaces normal in a radial direction with respect to a center of the rotatable, disposable device.

2. The blood testing apparatus from claim 1, wherein the lancing element remains in the test means following the lancing procedure and can be removed with the test means from an operating position in order to position a new test means there.

3. The blood testing apparatus from claim 1 wherein the lancing element is manageably conjoined to the test means and can be inserted together with the test means into the apparatus and can be deployed to an operating position.

4. The blood testing apparatus from claim 1, wherein spent lancing elements and test means can be ejected or brought to a storage and disposal position.

5. The blood testing apparatus claim 1, wherein the apparatus has an essentially circular disc-shaped outer contour.

6. The blood testing apparatus from claim 1, characterized by a safety mechanism which permits initiation of the lancing procedure only when the apparatus is manipulated correctly.

7. The blood testing apparatus from claim 1, wherein the number of test means to be manipulated as a unit is 5 to 75.

8. The blood testing apparatus from claim 1, wherein the number of test means to be manipulated as a unit is 14-28.

9. The blood testing apparatus from claim 1, wherein the at least one lancing element is disposed on the rotatable, disposable device.

10. The blood testing apparatus from claim 9, wherein the rotatable, disposable device comprises a first housing section for the test means and a second housing section for the at least one lancing elements.

11. The blood testing apparatus from claim 9, wherein the rotatable, disposable device has a central recess which has a drive mechanism and an electric-motor propulsion means for one of a carrier and the drive mechanism.

12. The blood testing apparatus from claim 9, wherein the rotatable, disposable device has a spring means to retract the at least one lancing element from the skin surface of the user.

13. The blood testing apparatus from claim 1, wherein the apparatus has oppositely located a lancing position against which to place the skin surface to be lanced and a release position to initiate the lancing procedure by manual actuation of a release button.

14. The blood testing apparatus from claim 13, wherein the apparatus is adapted to be held by a user holding the apparatus at the lancing position and the release button with two fingers.

15. The blood testing apparatus from claim 13, wherein the release button is ergonomically shaped to be grasped by the thumb of a user.

16. The blood testing apparatus from claim 13, wherein the release button has a pressure point which must be overcome in order to release the lancing element.

* * * * *